(12) United States Patent
Szczepankiewicz et al.

(10) Patent No.: US 11,939,348 B2
(45) Date of Patent: *Mar. 26, 2024

(54) COMPOSITIONS COMPRISING A PHOSPHORUS DERIVATIVE OF NICOTINAMIDE RIBOSIDE AND METHODS FOR MODULATION OF NICOTINAMIDE ADENINE DINUCLEOTIDE

(71) Applicant: Metro International Biotech, LLC, Worcester, MA (US)

(72) Inventors: Bruce Szczepankiewicz, Worcester, MA (US); James M. McKearin, Worcester, MA (US)

(73) Assignee: Metro International Biotech, LLC, Worcester, MA (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/440,849

(22) PCT Filed: Mar. 18, 2020

(86) PCT No.: PCT/US2020/023318
§ 371 (c)(1),
(2) Date: Sep. 20, 2021

(87) PCT Pub. No.: WO2020/197882
PCT Pub. Date: Oct. 1, 2020

(65) Prior Publication Data
US 2022/0144880 A1    May 12, 2022

Related U.S. Application Data

(63) Continuation-in-part of application No. 16/362,130, filed on Mar. 22, 2019, now Pat. No. 10,618,927.

(60) Provisional application No. 62/822,456, filed on Mar. 22, 2019.

(51) Int. Cl.
*C07H 19/048* (2006.01)
*C07H 21/02* (2006.01)

(52) U.S. Cl.
CPC .......... *C07H 19/048* (2013.01); *C07H 21/02* (2013.01)

(58) Field of Classification Search
None
See application file for complete search history.

(56) References Cited

U.S. PATENT DOCUMENTS

| | | |
|---|---|---|
| 3,201,389 A | 8/1965 | Fujimoto et al. |
| 3,451,997 A | 6/1969 | Fujimoto et al. |
| 4,411,995 A | 10/1983 | Whitesides et al. |
| 7,560,442 B2 | 7/2009 | Susilo |
| 7,776,326 B2 | 8/2010 | Milbrandt et al. |
| 7,977,049 B2 | 7/2011 | Sinclair et al. |
| 8,481,711 B2 | 7/2013 | Kaminishi et al. |
| 9,169,209 B2 | 10/2015 | Bair et al. |
| 9,295,688 B2 | 3/2016 | Milbrandt et al. |
| 9,458,172 B2 | 10/2016 | Bair et al. |
| 9,676,721 B2 | 6/2017 | Bair et al. |
| 9,822,129 B2 | 11/2017 | Bair et al. |
| 9,855,289 B2 | 1/2018 | Normington et al. |
| 9,861,651 B2 | 1/2018 | Brown et al. |
| 9,919,003 B2 | 3/2018 | Normington et al. |
| 9,975,915 B1 | 5/2018 | Migaud et al. |
| 10,000,519 B2 | 6/2018 | Migaud et al. |
| 10,214,552 B2 | 2/2019 | Fu et al. |
| 10,233,208 B1 | 3/2019 | Carr et al. |
| 10,392,415 B2 | 8/2019 | Livingston et al. |
| 10,392,416 B2 | 8/2019 | Livingston et al. |
| 10,548,913 B2 | 2/2020 | Normington et al. |
| 10,618,927 B1 | 4/2020 | Szczepankiewicz et al. |
| 11,059,847 B2 | 7/2021 | Livingston et al. |
| 11,180,521 B2 | 11/2021 | Kremsky et al. |
| 11,464,796 B2 | 10/2022 | Normington et al. |
| 2004/0224039 A1 | 11/2004 | Brucker |
| 2008/0318892 A1 | 12/2008 | Pickering et al. |
| 2012/0107888 A1 | 5/2012 | Schmalisch et al. |
| 2012/0328526 A1 | 12/2012 | Kristian |
| 2013/0102771 A1 | 4/2013 | Kaminishi et al. |
| 2013/0273034 A1 | 10/2013 | Bair et al. |

(Continued)

FOREIGN PATENT DOCUMENTS

| | | |
|---|---|---|
| CN | 101497638 A | 8/2009 |
| CN | 101601679 B | 8/2011 |

(Continued)

OTHER PUBLICATIONS

Liu et al. Nucleic Acids Research (1995), vol. 23, pp. 3742-3749.*
"Cardiac Medications," Heart.org, http://www.heart.org/en/health-topics/heart-attack/treatment-of-a-heart-attack/cardiac-medications (2015).
"Diabetes Treatment," Drugs.com, https://www.drugs.com/diabetes-treatment.html (2018).
"Medications for Dermatitis," Drugs.com, https://www.drugs.com/condition/dermatitis.html (2018).
"Medications for Obesity," Drugs.com, https://www.drugs.com/condition/obesity.html (2018).
"Medications for Peripheral Neuropathy," Drugs.com, https://www.drugs.com/condition/peripheral-neuropathy.html (2018).
"Medications for Thrombotic/Thromboembolic Disorder," Drugs.com, https://www.drugs.com/condition/thrombotic-thromboembolic-disorder.html (2018).

(Continued)

*Primary Examiner* — Patrick T Lewis
(74) *Attorney, Agent, or Firm* — Foley Hoag LLP; David P. Halstead; Benjamin A. Vaughan

(57) ABSTRACT

The invention relates to compounds and compositions for modulation of nicotinamide adenine dinucleotide (NAD+). The invention also relates to methods of making such compounds and compositions. The invention relates to pharmaceutical compositions containing one or more NAD+ modulating compounds as a first ingredient in combination with one or more active pharmaceutical ingredients. Further, the invention relates to methods of using such compounds or compositions to promote the increase of intracellular levels of nicotinamide adenine dinucleotide (NAD+) in cells and tissues for treating diseases and/or improving cell and tissue survival.

19 Claims, 1 Drawing Sheet

(56) References Cited

U.S. PATENT DOCUMENTS

| | | |
|---|---|---|
| 2013/0295051 A1 | 11/2013 | Bair et al. |
| 2014/0275057 A1 | 9/2014 | Bair et al. |
| 2014/0294805 A1 | 10/2014 | Bair et al. |
| 2015/0104384 A1 | 4/2015 | Bair et al. |
| 2015/0132280 A1 | 5/2015 | Lopez et al. |
| 2015/0175621 A1 | 6/2015 | Bair et al. |
| 2015/0258052 A1 | 9/2015 | Evans et al. |
| 2016/0002266 A1 | 1/2016 | Bair et al. |
| 2016/0022712 A1* | 1/2016 | Imai .................... A61P 3/06 514/52 |
| 2016/0168184 A1 | 6/2016 | Migaud et al. |
| 2016/0287621 A1 | 10/2016 | Sinclair et al. |
| 2016/0333041 A1 | 11/2016 | Fu et al. |
| 2016/0355514 A1 | 12/2016 | Bair et al. |
| 2016/0355539 A1 | 12/2016 | Migaud et al. |
| 2017/0066724 A1 | 3/2017 | Evans et al. |
| 2017/0182076 A1 | 6/2017 | Alvarez et al. |
| 2017/0189433 A1 | 7/2017 | Szczepankiewicz et al. |
| 2017/0204131 A1 | 7/2017 | Szczepankiewicz et al. |
| 2017/0210774 A1 | 7/2017 | Carlson et al. |
| 2017/0216262 A1 | 8/2017 | Bair et al. |
| 2017/0267709 A1 | 9/2017 | Migaud et al. |
| 2017/0304338 A1 | 10/2017 | Dellinger et al. |
| 2017/0368039 A1 | 12/2017 | Kenneth et al. |
| 2018/0030079 A1 | 2/2018 | Carlson et al. |
| 2018/0051253 A1 | 2/2018 | Chen |
| 2018/0086783 A1 | 3/2018 | Carlson et al. |
| 2018/0104248 A1 | 4/2018 | Lopez et al. |
| 2018/0134743 A1 | 5/2018 | Migaud et al. |
| 2018/0147227 A1 | 5/2018 | Normington et al. |
| 2018/0162895 A1 | 6/2018 | Fu et al. |
| 2018/0186824 A1 | 7/2018 | Migaud et al. |
| 2018/0228824 A1 | 8/2018 | Yoshino et al. |
| 2020/0031860 A1 | 1/2020 | Sauve |
| 2020/0157136 A1 | 5/2020 | Livingston et al. |
| 2020/0181188 A1 | 6/2020 | Rhonemus et al. |
| 2020/0352966 A1 | 11/2020 | Normington et al. |
| 2020/0368198 A1 | 11/2020 | Wu et al. |
| 2021/0030908 A1 | 2/2021 | Mason |
| 2022/0098229 A1 | 3/2022 | Livingston et al. |
| 2022/0144880 A1 | 5/2022 | Szczepankiewicz et al. |
| 2023/0158053 A1 | 5/2023 | Normington et al. |
| 2023/0257412 A1 | 8/2023 | Kremsky et al. |

FOREIGN PATENT DOCUMENTS

| | | |
|---|---|---|
| CN | 102876759 A | 1/2013 |
| CN | 104367587 B | 6/2018 |
| JP | S41-12737 B2 | 7/1966 |
| JP | S41-15179 B2 | 8/1996 |
| WO | WO-2006/072809 A2 | 7/2006 |
| WO | WO-2010/135520 A1 | 11/2010 |
| WO | WO-2012004917 A1 | 1/2012 |
| WO | WO-2012031196 A1 | 3/2012 |
| WO | WO-2012031197 A1 | 3/2012 |
| WO | WO-2012031199 A1 | 3/2012 |
| WO | WO-2012/094343 A1 | 7/2012 |
| WO | WO-2012/150952 A1 | 11/2012 |
| WO | WO-2013/085555 A2 | 6/2013 |
| WO | WO-2013127266 A1 | 9/2013 |
| WO | WO-2013127267 A1 | 9/2013 |
| WO | WO-2013127268 A1 | 9/2013 |
| WO | WO-2013127269 A1 | 9/2013 |
| WO | WO-2013130943 A1 | 9/2013 |
| WO | WO-2014/059034 A2 | 4/2014 |
| WO | WO-2014/074715 A1 | 5/2014 |
| WO | WO-2014/111906 A1 | 7/2014 |
| WO | WO-2014/146044 A1 | 9/2014 |
| WO | WO-2015/014722 A1 | 2/2015 |
| WO | WO-2015/069860 A1 | 5/2015 |
| WO | WO-2015073576 A1 | 5/2015 |
| WO | WO-2015/138969 A1 | 9/2015 |
| WO | WO-2015/186068 A1 | 12/2015 |
| WO | WO-2016014927 A2 | 1/2016 |
| WO | WO-2016086860 A1 | 6/2016 |
| WO | WO-2016/144660 A1 | 9/2016 |
| WO | WO-2016196941 A1 | 12/2016 |
| WO | WO-2017022768 A1 | 2/2017 |
| WO | WO-2017/059249 A1 | 4/2017 |
| WO | WO-2017/062311 A1 | 4/2017 |
| WO | WO-2017/079195 A1 | 5/2017 |
| WO | WO-2017110317 A1 | 6/2017 |
| WO | WO-2017/114796 A1 | 7/2017 |
| WO | WO-2017145151 A1 | 8/2017 |
| WO | WO-2017/161165 A1 | 9/2017 |
| WO | WO-2017185549 A1 | 11/2017 |
| WO | WO-2017/218580 A1 | 12/2017 |
| WO | WO-2018023205 A1 | 2/2018 |
| WO | WO-2018023207 A1 | 2/2018 |
| WO | WO-2018023208 A1 | 2/2018 |
| WO | WO-2018023209 A1 | 2/2018 |
| WO | WO-2018023210 A1 | 2/2018 |
| WO | WO-2018/047715 A1 | 3/2018 |
| WO | WO-2018/047716 A1 | 3/2018 |
| WO | WO-2018/052019 A1 | 3/2018 |
| WO | WO-2018/052020 A1 | 3/2018 |
| WO | WO-2018/089830 A1 | 5/2018 |
| WO | WO-2018/132833 A1 | 7/2018 |
| WO | WO-2018120069 A1 | 7/2018 |
| WO | WO-2018/143258 A1 | 8/2018 |
| WO | WO-2019/152416 A1 | 8/2019 |
| WO | WO-2020/197882 A1 | 10/2020 |
| WO | WO-2022/251491 A1 | 12/2022 |

OTHER PUBLICATIONS

"Sleep Disorders: Medications for Circadian Rhythm Disorders," WebMD, https://www.webmd.com/sleep-disorders/circadian-rhythm-disorder-medications#1 (2018).

"Wound Care Medications," GoodRx.com, https://www.goodrx.com/wound-care/drugs (2018).

Ahmadibeni et al., "Solid-Phase Synthesis of Symmetrical 5',5'-Dinucleoside Mono-, Di-, Tri-, and Tetraphosphodiesters," Organic Letters, 9(22): 4483-4486 (2007).

Anastasi et al., "New antiviral nucleoside prodrugs await application," Current medicinal chemistry, 10(18):1825-1843 (2003).

Asher et al., "SIRT1 Regulates Circadian Clock Gene Expression through PER2 Deacetylation," Cell, 134:317 (2008).

Atkinson et al., "Nicotinamide 6-Mercaptopurine Dinucleotide and Related Compounds: Potential Sources of 6-Mercaptopurine Nucleotide in Chemotherapy," Nature, 196: 35-36 (1962).

Barnea et al., "High-Fat Diet Delays and Fasting Advances the Circadian Expression of Adiponectin Signaling Components in Mouse Liver," Endicrinology 150:161 (2009).

Bauer, "Polymorphism—A Critical Consideration in Pharmaceutical Development, Manufacturing, and Stability," Journal of Validation of Technology, 14(5):15-23 (2008).

Bazzanini et al., "Synthetic approaches to a mononucleotide prodrug of cytarabine," Nucleosides, Nucleotides, and Nucleic Acids, 24(10-12):1635-1649 (2005).

Belenky et al., "Nicotinamide riboside promotes Sir2 silencing and extends lifespan via Nrk and Urh1/Pnp1/Meu1 pathways to NAD+," Cell,129(3):473-484 (2007).

Berghaeuser et al., "A Simple Preparation of an Enzyme Reactor Producing Nicotinamidemononucleotide," Biotechnology Letters, 3(7): 339-344 (1981).

Bieganowski et al., "Discoveries of nicotinamide riboside as a nutrient and conserved NRK genes establish a preiss-handler independent route to NAD+ in fungi and humans," Cell, 117:495-502 (2004).

Bobeck et al., "Advances in nucleoside monophosphate prodrugs as anti-HCV agents," Antiviral Therapy—An Official Publication of the International Society for Antiviral Research, 15(7):935-950 (2010).

Bordone et al., "Calorie restriction, SIRT1 and metabolism: understanding longevity," Nat Rev Mol Cell Biol, 6:298-305 (2005).

Borradaile et al., "NAD+, Sirtuins, and Cardiovascular Disease," Current Pharmaceutical Design, 15(1):110-117 (2016).

(56) References Cited

OTHER PUBLICATIONS

Brittain et al., "X-Ray Diffraction of Pharmaceutical Materials," Profiles of Drug Substances, Excipients, and Related Methodology, 30:273-319 (2003).
Byrn et al., "Pharmaceutical solids: a strategic approach to regulatory considerations," Pharmaceut Res, 12(7):945-954 (1995).
Caira, "Crystalline Polymorphism of Organic Compounds," Topics in Current Chemistry, 198:163-208 (1998).
CAS Registry No. 108273-23-0 (1987).
CAS Registry No. 108489-22-1 (1987).
CAS Registry No. 1094-61-7 (1984).
CAS Registry No. 150035-58-8 (1993).
CAS Registry No. 906748-40-1 (2006).
Cayman Chemical, "beta-Nicotinamide mononucleotide," Item No. 16411 Product Information (2014).
Cherney, "Osteoarthritis Medications List," Healthline, https://www.healthline.com/health/osteoarthritis/medications-list#nsaids (2016).
Cho et al., "Efficient synthesis of nucleoside aryloxy phosphoramidate prodrugs utilizing benzyloxycarbonyl protection," Tetrahedron, 67(30): 14 pages (2011).
Congiatu et al., "Novel potential anticancer naphthyl phosphoramidates of BVdU: separation of diastereoisomers and assignment of the absolute configuration of the phosphorus center," Journal of medicinal chemistry, 49(2): 452-455 (2006).
Corda et al., "Functional aspects of protein mono-ADP-ribosylation," EMBO J, 22(9):1953-1958 (2003).
Cross et al., "Rules for the Nomenclature of Organic Chemistry. Section E: Sterohemistry," Pure Appl Chem, 45(1):11-30, (1976).
Database Registry Chemical Abstracts, Database Accession No. 807266-77-9, CAS Registry No. 807266-77-9 (Jan. 2, 2005).
Dekker, Polymorphism in Pharmaceutical Solids, First Ed, pp. 184-208 (1999).
Dekker, Polymorphism in Pharmaceutical Solids, First Ed, pp. 7-8 (1999).
Dowden et al., "Chemical Synthesis of the Novel CA 2+ Messenger NAADP," Nucleosides, Nucleotides and Nucleic Acids, 24(5-7):513-518 (2005).
Erion et al., "Design, Synthesis, and Characterization of a Series of Cytochrome P450 3A-Activated Prodrugs (HepDirect Prodrugs) Useful for Targeting Phosph(on)ate-Based Drugs to the Liver," JACS Articles, 126: 5154-5163 (2004).
Extended European Search Report for EP Application No. 16833957.0 dated Dec. 21, 2018.
Extended European Search Report received for EP Patent Application No. EP 16852711, dated Feb. 11, 2019.
Fang et al., "Defective Mitophagy in XPA via PARP-1 Hyperactivation and NAD+/SIRT1 Reduction," Cell, 157(4):882-896 (2014).
Garten et al., "Nampt: Linking NAD biology, metabolism, and cancer," Trends Endocrinol Metab, 20(3):130-138 (2009).
Gavande et al., "DNA repair targeted therapy: The past or future of cancer treatment?," Pharmacology & Therapeutics, 160:65-83 (2016).
Gockel et al., "Synthesis of an oligonucleotide with a nicotinamide mononucleotide residue and its molecular recognition in DNA helices," Organic & Biomolecular Chemistry, 13(41):10303-10309 (2015).
Gomes et al., "Declining NAD+ Induces a Pseudohypoxic State Disrupting Nuclear-Mitochondrial Communication druing Aging," Cell, 155(7):1624-1638 (2013).
Guest et al., "Changes in Oxidative Damage, Inflammation and [NAD(H)] with Age in Cerebrospinal Fluid," PLOS One, 9(1):e85335 (2014).
Harrison et al., "Inhibition of Platelet Aggregation and the Platelet Release Reaction by alpha, omega Diadenosine polyphosphates," FEBS Letts 54(1):57-60 (1975).
Hecker et al., "Prodrugs of Phosphates and Phosphonates," Journal of Medicinal Chemistry, 51(8):2328-2345 (2008).
Hirayama, Yuukikagoubutsu Kessyo sakusei Handbook—Genri to Know-how—(Handbook for Preparation of Crystals of Organic Compounds—Principle and Know-how–), Maruzen Co. Ltd., pp. 37-84 (2008).
Imai et al., "NAD+ and sirtuins in aging and disease," Trends in Cell Biol, 24(8):464-471 (2014).
Imai et al., "Transcriptional silencing and longevity protein Sir2 is an NAD-dependent histone deacetylase," Nature, 403:795-800 (2000).
International Search Report and Written Opinion for International Application No. PCT/US2016/045855 dated Nov. 14, 2016.
International Search Report and Written Opinion for International Application No. PCT/US2016/054776 dated Jan. 25, 2017.
International Search Report and Written Opinion for International Application No. PCT/US2019/015672 dated May 15, 2019.
International Search Report and Written Opinion for International Application No. PCT/US2020/023318 dated Jun. 24, 2020.
Kohsaka et al., "high-Fat Diet Disrupts Behavioral and Molecular Circadian Rhythms in Mice," Cell Metab, 6:414 (2007).
Lee et al., "A Chemical Synthesis of Nicotinamide Adenine Dinucleotide (NAD+)," Chemical Communications (Cambridge), 8: 729-730 (1999).
Lee, "A practical guide to pharmaceutical polymorph screening & selection," Asian Journal of Pharmaceutical Science 9(4):163-175 (2014).
Lin et al., "Nicotinamide adenine dinucleotide, a metabolic regulator of transcription, longevity and disease," Curr Opin Cell Biol, 15:241-246 (2003).
Liu et al., "A Novel Preparation of Nicotinamide Mononucleotide," Nucleosides & Nucleotides, 13(5): 1215-1216 (1994).
Liu et al., "Enzymatic synthesis of polymers containing nicotinamide mononucleotide," Nucleic Acids Research, 23(18):3742 (1995).
Liu et al., "Synthesis of Phosphodiester-type Nicotinamide Adenine Dinucleotide Analogs," Tetrahedron, 65(40): 8378-8383 (2009).
Makarov et al., "Syntheses and chemical properties of β-nicotinamide riboside and its analogues and derivatives," Beilstein J Org Chem 15:401-430 (2019).
McGuigan et al., "Certain phosphoramidate derivatives of dideoxy uridine (ddU) are active against HIV and successfully by-pass thymidine kinase," FEBS Letters, 351: 11-14 (1994).
McGuigan et al., "Phosphorodiamidates as a Promising New Phosphate Prodrug Motif for Antiviral Drug Discovery: Application to Anti-HCV Agents," Journal of Medicinal Chemistry, 54: 8632-8645 (2011).
Menissier de Murcia et al., "Functional Interaction between PARP-1 and PARP-2 in chromosome stability and embryonic development in mouse," EMBO J, 22(9):2255-2263 (2003).
Migaud et al., "Probing Aplysia californica Adenosine 5'-Diphosphate Ribosyl Cyclase for Substrate Binding Requirements: Design of Potent Inhibitors," Biochemistry, 38:9105-9114 (1999).
Mikhailopulo et al., "Synthesis of glycosides of nicotinamide and nicotinamide mononucleotide," Synthesis, 5:388-389 (1981).
Moazed, "Enzymatic activities of Sir2 and chromatin silencing," Curr Opin Cell Biol, 13(2):232-238 (2001).
Montgomery et al., "Synthesis of Potential Anticancer Agents. XXVIII. Simple Esters of 6-Mercaptopurine Ribonucleotide2," The Journal of Organic Chemistry, 26(6):1929-1933 (1961).
Moynihan et al., "Increased dosage of mammalian Sir2 in pancreatic ß cells enhances glucose-stimulated insulin secretion in mice," Cell Metab, 2:105-117 (2005).
Nakahata et al., "The NAD+-Dependent Deacetylase SIRT1 Modulates CLOCK-Mediated Chromatin Remodeling and circadian Control," Cell, 134(2):329 (2008).
Nakai et al., Shin Seizaigaku (New Pharmacy), Nanzando Co. Ltd., 1st Edition, 2nd Printing, pp. 102-104, 217-236 (1984).
Nikiforov et al., "Pathways and Subcellular Compartmentation of NAD Biosynthesis in Human Cells," The Journal of Biological Chemistry, 286 (24): 21767-21778 (2011).
Park et al., "Nicotinamide Ribose 5'-0-[S-(3-Bromo-2-oxopropyl)] thiophosphate: A New Affinity Label for NMN Sites in Enzymes," Archives of Biochemistry and Biophysics, 303(2):483-488 (1993).
Pertusati et al., "Medicinal chemistry of nucleoside phosphonate prodrugs for antiviral therapy," Antivir Chem Chemother, 22(5):181-203 (2012).
Pfleiderer et al., "The mechanism of action of dehydrogenases. V. The adenosine diphosphate residue in nicotinamide-adenine dinucleotide (NAD)" Biochimica et Biophysica Acta, Specialized Section on Enzymological Subjects, 73(1): 39-49 (1963).

(56) References Cited

OTHER PUBLICATIONS

Pfleiderer et al., "Zum Wirkungsmechanismus von Dehydrogenasen V. Uber die Bedeutung des Adenosindiphosphatrestes im Nicotinamid-Adenin-Dinucleotid," Biochimica et Biophysica Acta, 73:39-49 (1963).
Pfleiderer et al., "Zum Wirkungsmechanismus von Dehydrogenasen. Das Reaktionsverhalten von Pyridinnucleotiden (PN) und PN-Modellen mit Sulfit als nucleophilem Agens," Chemische Berichte, 93(12):3083-3099 (1960).
Picard et al., "Sirt1 promotes fat mobilization in white adipocytes by repressing PPAR-y," Nature, 429:771-776 (2004).
Preitner et al., "The Orphan Nuclear Receptor REV-ERBa Controls Circadian Transcription within the Positive Limb of the Mammalian circadian Oscillator," Cell, 110:251 (2002).
Rajman et al., "Therapeutic Potential of NAD-Boosting Molecules: The In Vivo Evidence," Cell Metabolism, 27(3): 529-547 (2018).
Ramsey et al., "Cicadian clock feedback cycle through NAMPT-mediated NAD+ biosynthesis," Science, 324(5927):651-654 (2009).
Redpath et al., "Nicotinamide Benzimidazolide Dinucleotides Non-Cyclisable Analogues of NAD+," Synlett, 25:2331-2336 (2014).
Riemschneider et al., "Zur Beeinflussung von Stoffwechselvorgangen durch unphysiologische Verbindungen, IV: Nicotinylaminosaureester und Nucleosid-Deritvate," Insect repellent science, 41(3):99-106 (1976).
Rodgers et al., "Nutrient control of glucose homeostasis through a complex of PGC-1α and SIRT1," Nature, 434:113-118 (2005).
Rodionova et al., "Metabolic and bactericidal effects of targeted suppression of NadD and NadE enzymes in *Mycobacteria*," mBio, 5(1):e00747-13 (2014).
Roskar et al., "Analytical Methods for Quantification of Drug Metabolites in Biological Samples," IntechOpen, Chapter 4:79-126 (2012).
Rudic et al., "BMAL1 and Clock, Two Essential Components of the Circadian Clock, Are Involved in Glucose Homeostasis," PLoS Biol, 2:e377 (2004).
Rutter et al., "Regulation of Clock and NPAS2 DNA Binding by the Redox State of NAD Cofactors," Science, 293(5529):510 (2001).
Sarma et al., "Investigations of Inter- and Intramolecular Interactions in Flavin-Adenine Dinucleotide by Proton Magnetic Resonance," Biochemistry, 7(12):4359-4367 (1968).
Sato et al., "A Functional Genomics Strategy Reveals Rora as a Component of the Mammalian Circadian Clock," Neuron, 43:527 (2004).
Sharma et al., "X-ray diffraction: a powerful method of characterizing nanomaterials," Recent Research in Science and Technology, 4:77-79 (2012).
Shioji, Kokei Seizai no Seizo Gijutsu (Manufacture Technology of Solid Tablet), CMC Publishing Co. Ltd., Popular Edition, 1st Printing, pp. 9-14 (2003).
Smith et al., "A phylogenetically conserved NAD+-dependent protein decetylase activity in the Sir2 protein family," Proc Natl Acad Sci, 97(12):6658-6663 (2000).
Soto-Gamez et al., "Therapeytic interventions for aging: the case of cellular senescence," Drug Discovery Today, 22(5):786-795 (2017).
Stein et al., "Expression of nampt in hippocampal and cortical excitatory neurons is critical for cognitive function," J Neurosci, 34(17): 5800-5815 (2014).
Stein et al., "Scientific ablation on Nampt in adult neural stem cells recapitulates their functional defects during aging," EMBO J, 33(12):1321-1340 (2014).
Stieger et al., "7:Recrystallization of Active Pharmaceutical Ingredients," Crystallization—Science and Technology, 183-204 (2012).
Takahashi et al., "The Genetics of Mammalian Circadian Order and Disorder: Implications for Physiology and Disease," Nat Rev Genet, 9(10):764 (2008).
The Chemical Society of Japan Ed., 4th Edition Jikken Kagaku Kouza 1 Kihon Sousa I (4th Edition Experimental Chemistry 1 Basic Operation I), Maruzen Co. Ltd., 2nd Printing, pp. 184-186 (1996).

Thorpe et al., "Lipoamide Dehydrogenase from Pig Heart. Pyridine Nucleotide Induced Changes in Monoalkylated Two-Electron Reduced Enzyme," Biochemistry, 20: 1507-1513 (1981).
Turek et al., "Obesity and Metabolic Syndrome in Circadian Clock Mutant Mice," Science, 308:1043 (2005).
United States Department of Health and Human Services. "Guidance for Industry Pyrogen and Endotoxin Testing: Questions and Answers," pp. 1-10 (2012).
United States Pharmacopeia General Chapter <151> Pyrogen Test, Mar. 27, 2019, 2 pages.
Walt et al., "An Efficient Chemical and Enzymatic Synthesis of Nicotinamide Adenine Dinucleotide (NAD+)," Journal of the American Chemical Society, 106(1): 234-239 (1984).
Wang et al., "A local mechanism mediates NAD-dependent protection of axon degeneration," J Cell Biol, 170(3):349-355 (2005).
Wiemer et al., "Prodrugs of Phosphnates and Phosphates: Crossing the Membrane Barrier," Topics in Current Chemistry, 360:115-160 (2014).
Woenckhaus, "Synthesen und biochemische Eigenschaften wassertoffubertragender Coenzye modelle," Chemische Berichte, 97(9):2439-2446 (1964).
Yang et al., "NAD+-dependent Deacetylase SIRT3 Regulates Mitochondrial Protein Synthesis by Deacetylation of the Ribosomal Protein MRPL10," J Biol Chem, 285: 7417-7429 (2010).
Yoshino et al., "Nicotinamide Mononucleotide, a Key NAD+ Intermediate, Treats the Pathology of Diet- and Age-Induced Diabetes in Mice," Cell Metab, 14(4): 528-536 (2011).
ß-Nicotinamide Mononucleotide, Item No. 16411 Safety Data Sheet, Cayman Chemical (2015).
Cattaneo-Pangrazzi ., "The novel heterodinucleoside dimer 5-FdU-NOAC is a potent cytotoxic drug and a p53-independent inducer of apoptosis in the androgen-independent human prostate cancer cell lines PC-3 and DU-145", The Prostate 45(1): 8-18 (2000).
Chemical Cayman, "Nicotinic Acid Mononucleotide," Item No. 32883.
Huang et al., "Metabolomics-driven identification of adenosine deaminase as therapeutic target in a mouse model of Parkinson's disease," Journal of Neurochemistry, 150: 282-295 (2019).
International Search Report and Written Opinion for International Application No. PCT/US22/031124 dated Oct. 6, 2022.
Invitation to Pay Additional Fees for International Application No. PCT/US22/31124 dated Aug. 5, 2022.
Kamel et al., "Pharmaceutical significance of cellulose: A review", Express Polym Letters 2(11): 758-778 (2008).
Leisvuori et al. "5', 5'-Phosphodiesters and esterase labile triesters of 2'-C methylribonucleosides", ARKIVOC: Online Journal of Organic Chemistry (2012).
Pencina et al., "MIB-626, an Oral Formulation of a Microcrystalline Unique Polymorph of Beta-Nicotinamide Mononucleotide, Increases Circulating Nicotinamide Adenine Dinucleotide and its Metabolome in Middle-Aged and Older Adults", J Gerontol A Biol Sci Med Sci, 2023, vol. 78, No. 1, 90-96.
Pencina et al., "Nicotinamide Adenine Dinucleotide Augmentation in Overweight or Obese Middle-Aged and Older Adults: A Physiologic Study", The Journal of Clinical Endocrinology & Metabolism, Feb. 6, 2023, 00, pp. 1-13.
Petrelli et al., "NMN/NaMN Adenylyltransferase (NMNAT) and NAD Kinase (NADK) Inhibitors: Chemistry and Potential Therapeutic Applications," Current Medicinal Chemistry, 18: 1973-1992 (2011).
PubChem SID: 347731451 "Substance Record 321-02-8" retrieved online <https://pubchem.ncbi.nlm.nih.gov/substance/347731451>: 6 pages (Create Date Oct. 23, 2017).
Puech et al.,"Nucleotidic prodrugs of anti-HIV dideoxynucleosides", Bioorganic & medicinal chemistry letters 2(6): 603-606 (1992).
ADP PubChem SID 134971804 deposited on Mar. 21, 2012.
AMP PubChem SID 134970876 deposited on Mar. 21, 2012.
ATP PubChem SID 134972915 deposited on Mar. 21, 2012.
Eliseev et al., "Comparative study of antihypoxic properties of some nucleosides and nucleotides." *Pharmaceutical Chemistry Journal* 20.3 (1986): 160-162.

(56) References Cited

OTHER PUBLICATIONS

Galli et al., "The Nicotinamide Phosphoribosyltransferase: A Molecular Link between Metabolism, Inflammation, and Cancer", Cancer Research, 70(1), pp. 8-11, 2010.
Hardie, "Minireview: the AMP-activated protein kinase cascade: the key sensor of cellular energy status", *Endocrinology* 144(12): 5179-5183 (2003).
Yamamoto et al., "Nicotinamide mononucleotide, an intermediate of NAD+ synthesis, protects the heart from ischemia and reperfusion", PloS one 9.6: e98972 (2014).

* cited by examiner

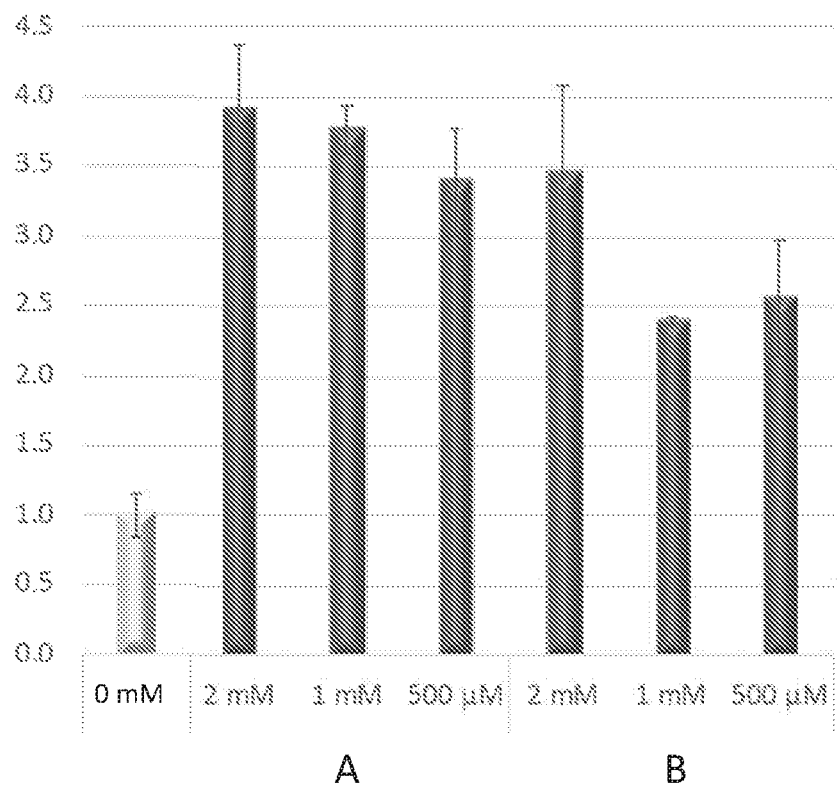

COMPOSITIONS COMPRISING A PHOSPHORUS DERIVATIVE OF NICOTINAMIDE RIBOSIDE AND METHODS FOR MODULATION OF NICOTINAMIDE ADENINE DINUCLEOTIDE

RELATED APPLICATIONS

This application is the U.S. national phase of International Application No. PCT/US2020/023318, filed Mar. 18, 2020, which claims priority to U.S. Provisional Application No. 62/822,456, filed Mar. 22, 2019, and U.S. Non-Provisional application Ser. No. 16/362,130, filed Mar. 22, 2019, each of which is incorporated herein by reference in its entirety.

BACKGROUND

Nicotinamide adenine dinucleotide (NAD) and related compounds are known as essential coenzymes in cellular redox reactions in all living organisms. Several lines of evidence have also shown that NAD participates in a number of important signaling pathways in mammalian cells, including poly(ADP-ribosyl)ation in DNA repair (Menissier de Murcia et al., EMBO J., (2003) 22, 2255-2263), mono-ADP-ribosylation in the immune response and G protein-coupled signaling (Corda and Di Girolamo, EMBO J., (2003) 22, 1953-8), and the synthesis of cyclic ADP-ribose and nicotinate adenine dinucleotide phosphate (NAADP) in intracellular calcium signaling (Lee, Annu. Rev. Pharmacol. Toxicol., (2001) 41, 317-345). It has also been shown that NAD and its metabolites play an important role in transcriptional regulation (Lin and Guarente, Curr. Opin. Cell. Biol., (2003) 15, 241-246). In particular, the discovery of Sir2 NAD-dependent deacetylase activity (e.g., Imai et al., Nature, (2000) 403, 795-800; Landry et al., Biochem. Biophys. Res. Commun., (2000) 278, 685-690; Smith et al., Proc. Natl. Acad. Sci. USA, (2000) 97, 6658-6663) drew attention to this role of NAD.

Despite the advances in understanding the biology of NAD, there remains a need for improved compositions and methods of using such compositions for pharmacologic intervention and/or manipulation of the NAD pathway in living cells and tissues.

SUMMARY

The invention relates to compounds and compositions for modulation of nicotinamide adenine dinucleotide (NAD+). In some embodiments, the invention relates to methods of making such compounds and compositions. In some embodiments, the invention relates to pharmaceutical compositions containing one or more NAD+ modulating compounds as a first ingredient in combination with one or more active pharmaceutical ingredients. In further embodiments, the invention relates to methods of using such compounds or compositions to promote the increase of intracellular levels of nicotinamide adenine dinucleotide (NAD+) in cells and tissues for treating diseases and/or improving cell and tissue survival.

BRIEF DESCRIPTION OF THE DRAWINGS

FIG. 1 depicts NAD(H) normalized to total protein in treated AML12 cells compared to untreated cells (first data column normalized to 1.0) for Compound A at 2 mM, 1 mM and 500 micromolar concentrations, and for Compound B at 2 mM, 1 mM, and 500 micromolar concentrations, showing that both compounds possess NAD(H) boosting activity in AML12 cells. Compound A is Formula I, n=2. Compound B is Formula I, n=1.

DETAILED DESCRIPTION

Definitions

Unless defined otherwise, all technical and scientific terms used herein have the meaning commonly understood by a person skilled in the art of the present disclosure. As used herein, the following terms have the meanings ascribed to them below, unless specified otherwise.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "purified," as described herein, refers to the purity of a given compound. For example, a compound is "purified" when the given compound is a major component of the composition, i.e., at least about 50% w/w pure. Thus, "purified" embraces at least about 50% w/w purity, at least about 60% w/w purity, at least about 70% purity, at least about 80% purity, at least about 85% purity, at least about 90% purity, at least about 92% purity, at least about 94% purity, at least about 96% purity, at least about 97% purity, at least about 98% purity, at least about 99% purity, at least about 99.5% purity, and at least about 99.9% purity, wherein "substantially pure" embraces at least about 97% purity, at least about 98% purity, at least about 99% purity, at least about 99.5% purity, and at least about 99.9% purity.

The term "metabolite," as described herein, refers to a compound produced in vivo after administration to a subject.

The term "salts," as described herein, refers to a compound comprising a cation and an anion, which can be produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_gR_{4-g}^+$, in which R is a $C_{1-3}$ alkyl and g is a number selected from 0, 1, 2, 3, or 4. It should be understood that all references to pharmaceutically acceptable salts include solvent addition forms (solvates) or crystal forms (polymorphs) as defined herein, of the same acid addition salt.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

Compounds, Compositions and Methods of Treatment

Provided herein is a compound having the structure:

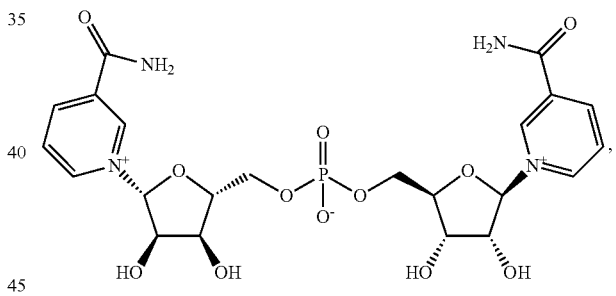

and salts thereof.

Also provided herein are compositions comprising one or more pharmaceutically acceptable excipients and one or more compounds, and/or salts, thereof, wherein the compound has a structure represented by Formula I:

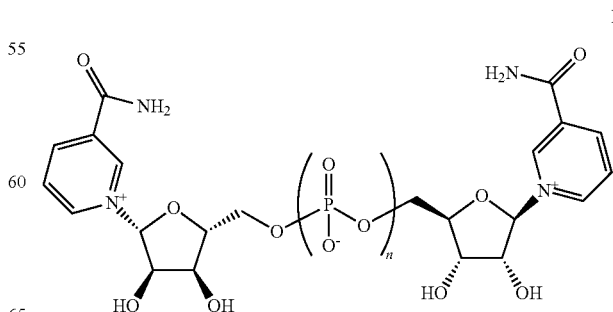

wherein n is an integer from 1 to 3.

Provided herein are compositions comprising one or more additional active pharmaceutical ingredients and one or more compounds, and/or one or more salts thereof, wherein the compound has a structure represented by Formula I:

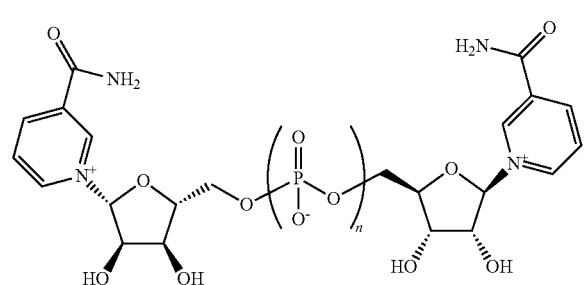

wherein n is an integer from 1 to 3.

In some embodiments, n is 1. In other embodiments, n is 2. In yet other embodiments, n is 3.

In some embodiments, the composition is in a solid form selected from a tablet, a pill, a capsule, a caplet, a troche, granules, powders, sachet, dry powder inhalation form, a chewable, a pastille, and a lozenge. In certain embodiments, the composition is in the form of a tablet. In other embodiments, the composition is in a form of a hard or soft gelatin capsule.

In some embodiments, the compound is in an amorphous solid form. In other embodiments, the compound is in a crystalline solid form.

In some embodiments, the amount of the compound of Formula I in the composition is about 0.001% by weight to about 10% by weight, about 0.01% by weight to about 10% by weight, about 0.1% by weight to about 8% by weight, about 0.25% by weight to about 8% by weight, about 0.5% by weight to about 5% by weight, about 0.5% by weight to about 3% by weight, or about 0.1% by weight to about 1% by weight, preferably about 0.5% by weight of the composition. In certain embodiments, the amount of the compound of Formula I in the composition is about 0.25% by weight of the composition.

In some embodiments, the pharmaceutically acceptable excipient is selected from an anti-adherent, binder, coating, dye, disintegrant, flavoring agent, glidant, lubricant, preservative, sorbent, sweetener, syrups, elixirs, dispersant, diluent, filler, granulating agent, coating agent, wax, suspending agent, wetting agent, thickener and vehicle and combinations thereof. In some embodiments, the excipient is a solid excipient.

In some embodiments, the pharmaceutically acceptable excipient is present in an amount of at least about 5% by weight, at least about 10% by weight, at least about 15% by weight, at least about 20% by weight, at least about 25% by weight, at least about 30% by weight, at least about 35% by weight, at least about 40% by weight, at least about 45% by weight, at least about 50% by weight, at least about 55% by weight, or at least about 60% by weight of the composition. In some embodiments, the pharmaceutically acceptable excipient is present in an amount of at least about 20% by weight, at least about 25% by weight, at least about 30% by weight, at least about 35% by weight, or at least about 40% by weight, preferably at least about 30% by weight of the composition. In other embodiments, the pharmaceutically acceptable excipient is present in an amount of at least about 50% by weight of the composition.

In some embodiments, the amount of the compound of Formula I relative to the amount of one or more additional active pharmaceutical ingredients in the composition ranges from about 0.001% by weight to less that about 50% by weight, about 0.01% by weight to about 45% by weight, about 0.05% by weight to about 40% by weight, about 0.1% by weight to about 30% by weight, about 0.5% by weight to about 30% by weight, about 1% by weight to about 30% by weight, about 1.5% by weight to about 20% by weight, about 2% by weight to about 20% by weight, about 2.5% by weight to about 20% by weight, about 3% by weight to about 20% by weight, or about 0.5% by weight to about 5% by weight, preferably about 0.5% by weight to about 1.5% by weight of the composition. In certain embodiments, the amount of the compound of Formula I relative to the amount of one or more additional active pharmaceutical ingredients in the composition is 0.5% by weight of the composition. In other embodiments, the amount of the compound of Formula I relative to the amount of one or more additional active pharmaceutical ingredients in the composition is 1.5% by weight of the composition.

In some embodiments, the amount of the compound of Formula I relative to the amount of one or more additional active pharmaceutical ingredients is greater than zero. The term "greater than zero" refers to an amount that is at the lower limit of detection by any quantitative means known in the art. Non-limiting examples of methods for quantifying a chemical substance include chromatography (liquid LC, high-performance liquid HPLC, gas G), electrospray ionization (ESI), atmospheric pressure chemical ionization (APCI), and atmospheric pressure photoionization (APPI). These separation methods are coupled to a mass analyzer that identifies the compound being measured. Mass spectrometry techniques include triple quadrupole (QQQ), ion trap (IT), triple quadrupole-linear ion traps (QTrap), time of flight (TOF), triple quadrupole-time of flight (Q-TOF), Orbitrap, and Fourier transform-ion cyclotron resonance (FT-ICR). See, Roskar, R. et al. *Analytical Methods for Quantification of Drug Metabolites in Biological Samples* 2012, pgs. 87-91.

In some embodiments, the active pharmaceutical ingredient is selected from compounds in the NAD+ pathway, such as nicotinic acid (NA), nicotinamide (Nam), nicotinamide mononucleotide (NMN), nicotinamide riboside (NR), nicotinic acid mononucleotide (NaMN), nicotinic acid riboside (NAR), nicotinamide adenine dinucleotide (NAD$^+$/NADH), nicotinamide adenine dinucleotide phosphate (NADP), and nicotinic acid adenine dinucleotide (NaAD). In some embodiments, the active pharmaceutical ingredient is an amorphous solid. In some embodiments, the active pharmaceutical ingredient is a crystalline solid. In some embodiments, the active pharmaceutical ingredient is amorphous NMN.

In some embodiments, the active pharmaceutical ingredient is selected from anti-aging compounds such as antioxidants (e.g., CoQ10, vitamin C, Vitamin E), peptides such as Matrixyl (palmitoyl pentapeptide-3), Argireline (acetyl hexapeptide-3), Vitamin A, related retinoids, and anti-aging sunscreens such as Helioplex and Mexoryl SX (ecamsule).

In some embodiments, the active pharmaceutical ingredient is selected from pain relievers and inflammation-reducing agents, such as acetaminophen, duloxetine, aspirin, ibuprofen, naproxen, diclofenac, and diclofenac-misoprostol. Other NSAID active pharmaceutical ingredients include celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, and mefenamic acid.

In some embodiments, the active pharmaceutical ingredient is selected from compounds used to treat dermatitis, such as triamcinolone, clobetasol, betamethasone, hydrocortisone, fluocinonide, and prednisolone. In other embodiments, the active pharmaceutical ingredient is selected from compounds used to treat wounds, such as silver sulfadiazine, santyl collagenase, chlorhexidine, urea, venelex, and levicyn.

In some embodiments, the active pharmaceutical ingredient is selected from senolytics such as dasatinib, quercetin, cortisol, corticosterone, metformin, resveratrol, apigenin, wogonin, kaempferol, rapamycin, ruxolitinib, tofacitinib, simvastatin, and navitoclax.

In some embodiments, the active pharmaceutical ingredient is selected from compounds used to treat cardiovascular diseases and disorders, such as amiloride, bumetanide, chlorothiazide, chlorthalidone, furosemide, hydro-chlorothiazide, indapamide, and spironolactone.

In some embodiments, the active pharmaceutical ingredient is selected from a serotonin reuptake inhibitor (SRI), a 5HT2 receptor antagonist, an anticonvulsant, a norepinephrine reuptake inhibitor, an alpha-adrenoreceptor antagonist, an NK-3 antagonist, an NK-1 receptor antagonist, a PDE4 inhibitor, an Neuropeptide Y5 Receptor Antagonists, a D4 receptor antagonist, a 5HT1A receptor antagonist, a 5HT1D receptor antagonist, a CRF antagonist, a monoamine oxidase inhibitor, and a sedative-hypnotic drug.

In some embodiments, the SRI is a selective SRI selected from fluoxetine, norfluoxetine, nefazodone, hydroxynefazodone, oxonefazodone, duloxetine, venlafaxine, milnacipran, citalopram, fluvoxamine, paroxetine and sertraline. In some embodiments, the sedative-hypnotic drug is selected from alprazolam, chlordiazepoxide, clonazepam, chlorazepate, clobazam, diazepam, halazepam, lorazepam, oxazepam prazepam, Zolpidem, and barbiturates. In some embodiments, the 5HT1A receptor antagonist is selected from buspirone, flesinoxan, gepirone and ipsapirone.

In certain embodiments, the norepinephrine reuptake inhibitor is selected from tertiary tricyclics such as amitriptyline, clomipramine, doxepin, imipramine and trimipramine. In other embodiments, the norepinephrine reuptake inhibitor is selected from secondary amine tricyclics such as amoxapine, desipramine, maprotiline, nortriptyline and protriptyline.

In some embodiments, the monoamine oxidase inhibitor is selected from isocarboxazid, phenelzine, tranylcypromine, selegiline and moclobemide.

In other embodiments, the active pharmaceutical ingredient is a chemotherapeutic agent selected from 1-amino-4-phenylamino-9,10-dioxo-9,10-dihydroanthracene-2-sulfonate (acid blue 25), 1-amino-4-[4-hydroxyphenylamino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, ABT-263, afatinib dimaleate, axitinib, aminoglutethimide, amsacrine, anastrozole, APCP, asparaginase, AZD5363, Bacillus Calmette-Guérin vaccine (bcg), bicalutamide, bleomycin, bortezomib, β-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzenesulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA).

In other embodiments, suitable chemotherapeutic agents include: ABT-263, dexamethasone, 5-fluorouracil, PF-04691502, romidepsin, and vorinostat (SAHA). In other embodiments, chemotherapeutic agents include: 1-amino-4-phenylamino-9,10-dioxo-9,10-dihydroanthracene-2-sulfonate (acid blue 25), 1-amino-4-[4-hydroxyphenylamino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, APCP, β-methylene-ADP (AOPCP), capecitabine, cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline.

Other types of chemotherapeutic agents include immuno-oncology agents such as abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab.

In some embodiments, the active pharmaceutical ingredient is selected from PARP inhibitors that are known to repair DNA damage, such as olaparib, veliparib, niraparib, NMS-P118, talazoparib, and rucaparib.

In some embodiments, the active pharmaceutical ingredient is selected from agents for treating neurodegenerative diseases such as amantadine, apomorphine, baclofen, carbidopa, dantrolene, donepezil, entacapone, galantamine, levodopa, memantine, pramipexole, rasagiline, riluzole, rivastigmine, ropinirole, selegiline, tacrine, tetrabenazine, tizanidine, and tolcapone.

In some embodiments, the active pharmaceutical ingredient is selected from agents for treating neuropathy, such as gabapentin, levocarnitine, duloxetine, carbamazepine, capsaicin, pregabalin, and qutenza.

In some embodiments, the active pharmaceutical ingredient is selected from agents for treating thrombotic disorders, such as heparin, Activase, alteplase, argatroban, Acova, urokinase, and Abbokinase.

In some embodiments, the active pharmaceutical ingredient is selected from agents for treating obesity and weight gain, such as phentermine, Adipex-P, topiramate, Belviq, Contrave, Desoxyn, Alli, phendimetrazine, Xenical, orlistat, and Tenuate.

In some embodiments, the active pharmaceutical ingredient is selected from agents for treating diabetes and regulating blood glucose levels, such as chlorpropamide, tolbutamide, tolazamide, glimepiride, glyburide, glipizide, gliclazide, metformin, miglitol, acarbose, pioglitazone, rosiglitazone, repaglinide, nateglinide, exenatide, liraglutide, dulaglutide, lixisenatide, semaglutide, saxagliptin, sitagliptin, linagliptin, alogliptin, canagliflozin, dapagliflozin, empagliflozin, and ertugliflozin.

In some embodiments, the active pharmaceutical ingredient is selected from agents for treating circadian rhythm disorders, such as melatonin, rozerem, benzodiazapines, Ambien, Sonata, Lunesta, Belsomra, and Provigil.

Also disclosed herein is a compound of Formula II:

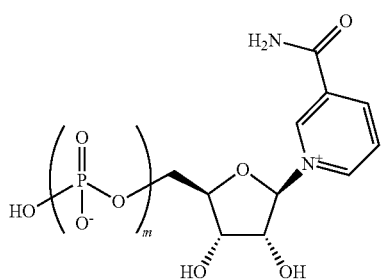

II wherein m is 2 or 3, or a salt thereof. In some embodiments, m is 2, while in other embodiments, m is 3.

In some embodiments, the one or more active pharmaceutical ingredients are selected from nicotinic acid (NA), nicotinamide (Nam), nicotinamide mononucleotide (NMN), nicotinamide riboside (NR), nicotinic acid mononucleotide (NaMN), nicotinic acid riboside (NAR), nicotinamide adenine dinucleotide ($NAD^+$/NADH), nicotinamide adenine dinucleotide phosphate (NADP), nicotinic acid adenine dinucleotide (NaAD), and one or more compounds of Formula II:

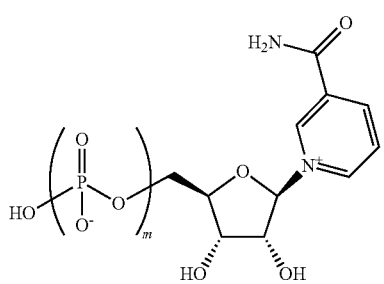

II wherein m is 2 or 3, and one or more salts thereof, and combinations thereof.

The present invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts.

In certain embodiments, the compound is a salt with an anion selected from acetate, triflate, halide, trifluoroacetate, or formate. In other embodiments, if the disclosed compound is in contact with a media, e.g., aqueous media, the anion can be selected from, for example, $OH^-$, $H_2PO_4^-$, $HPO_4^{2-}$, $HSO_4^-$, $SO_4^{2-}$, $NO_3^-$, $HCO_3^-$, and $CO_3^{2-}$.

In some embodiments, the disclosed compounds are in the form of a negatively charged phosphate, which may form a salt with any suitable cation. The cation can alter as the compound is isolated or transferred into media with different anionic species. For example, a disclosed compound may be in the form of a phosphate salt that is a pharmaceutically acceptable salt as described herein. In certain embodiments, the cation can be selected from $Li^+$, $Na^+$, $K^+$, $Mg^{2+}$, and $Ca^{2+}$.

Provided herein are methods of increasing NAD+ levels in a subject in need thereof, comprising administering a compound, or a salt thereof, wherein the compound is one disclosed herein.

Provided herein are methods of treating a disease or disorder associated with NAD+ biosynthesis, comprising administering a compound, or a salt thereof, wherein the compound is one disclosed herein.

Provided herein is any composition as described herein for use in increasing NAD+ levels. In one embodiment the composition comprises a compound of Formula I.

Diseases, Disorders and Conditions

Provided herein are methods for using the disclosed compounds and pharmaceutical compositions thereof. The disclosed compounds and pharmaceutical compositions thereof can be useful for a variety of therapeutic applications including, for example, treating and/or reducing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a disclosed compound and/or pharmaceutical composition thereof.

In other embodiments, the disclosed compounds and/or a pharmaceutical composition thereof can be used to treat skin conditions. Exemplary skin conditions that may be treated in accordance with the methods described herein include disorders or diseases associated with or caused by inflammation, sun damage, or natural aging. For example, the compositions find utility in the treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In other embodiments, the disclosed compounds and pharmaceutical compositions thereof may be used for the treatment of wounds and/or burns to promote healing, including, for example, first-, second- or third-degree burns and/or thermal, chemical or electrical burns.

The disclosed compounds and pharmaceutical compositions thereof can also be administered to a subject suffering from an acute disease, e.g., damage to an organ or tissue, e.g., a subject suffering from stroke or myocardial infarction or a subject suffering from a spinal cord injury. The disclosed compounds and pharmaceutical compositions thereof may also be used to repair an alcoholic's liver.

In certain embodiments, a compound or pharmaceutical composition as disclosed herein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In certain embodiments, a compound or pharmaceutical composition as disclosed herein may be administered to a subject in order to generally increase the lifespan of its cells and to protect its cells against stress and/or against apoptosis. Treating a subject with a compound described herein may be similar to subjecting the subject to hormesis, i.e., mild stress that is beneficial to organisms and may extend their lifespan.

In other embodiments, provided herein is a method for treating a cardiovascular disease by administering to a subject in need thereof a disclosed compound and/or a pharmaceutical composition thereof. Cardiovascular diseases that can be treated using the disclosed compounds and pharmaceutical compositions thereof include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated include those related to platelet aggregation, the retinal arterioles, the glomerular arterioles, the vasa nervorum, cardiac arterioles, and associated capillary beds of the eye, the kidney, the heart, and the central and peripheral nervous systems. The disclosed compounds and pharmaceutical compositions thereof may also be used for increasing HDL levels in plasma of an individual.

The disclosed compounds and pharmaceutical compositions thereof may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In other embodiments, the radiation or toxin exposure is received unintentionally, e.g., as a result of an industrial accident, habitation in a location of natural radiation, terrorist act, or act of war involving radioactive or toxic material. In such a case, the disclosed compounds and pharmaceutical compositions thereof are preferably administered as soon as possible after the exposure to inhibit apoptosis and the subsequent development of acute radiation syndrome.

In other embodiments, the disclosed compounds and pharmaceutical compositions thereof may be useful for treating age-related disorders, such as, for example, cancer. Exemplary cancers that may be treated using the disclosed compounds and pharmaceutical compositions thereof include those of the brain and kidney; hormone-dependent cancers including breast, prostate, testicular, and ovarian cancers; lymphomas, and leukemias. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of the disclosed compounds and pharmaceutical compositions thereof.

In some embodiments, the disclosed compounds and pharmaceutical compositions thereof can be used to treat patients suffering from neurodegenerative diseases, and traumatic or mechanical injury to the central nervous system (CNS) or peripheral nervous system (PNS). Examples of neurodegenerative diseases include, but are not limited to, ataxia, Alzheimer's disease (AD), Parkinson's disease (PD), Huntington disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies, and Friedreich's ataxia.

In other embodiments, the disclosed compounds and pharmaceutical compositions thereof may be used for reducing appetite and/or increasing satiety, thereby causing weight loss or avoidance of weight gain. A subject in need of such a treatment may be a subject who is overweight, obese or a subject likely to become overweight or obese.

In other embodiments, the disclosed compounds and pharmaceutical compositions thereof may be used to treat a subject who has cachexia or may be likely to develop cachexia. A method may further comprise monitoring in the subject the state of the disease. Methods for promoting appetite and/or weight gain may include, for example, prior identifying a subject as being in need of decreased fat or lipid metabolism, e.g., by weighing the subject, determining the BMI of the subject. The method may also include monitoring the subject, e.g., during and/or after administration of the disclosed compounds or pharmaceutical compositions thereof. The administering can include one or more dosages, e.g., delivered in boluses or continuously. Monitoring can include evaluating a hormone or a metabolite. Exemplary hormones include leptin, adiponectin, resistin, and insulin. Exemplary metabolites include triglycerides, cholesterol, and fatty acids.

In some embodiments, the disclosed compounds and pharmaceutical compositions thereof may be used for treating a metabolic disorder, such as insulin-resistance, a pre-diabetic state, type II diabetes, and/or complications thereof.

Administration of the disclosed compounds and pharmaceutical compositions thereof may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis, and lipodystrophy.

Provided herein is a process for regulating the concentration of blood glucose in a mammal. As utilized herein, regulating the concentration of blood glucose refers to any increase, decrease, and/or maintenance in or of the concentration of blood glucose as compared to a previously determined level.

The methods of treatment disclosed herein are also directed to methods of regulating the circadian clock, thereby regulating or affecting biological functions that are regulated by (sometimes also said to be affected by, affiliated with, or mediated by) the activity of the circadian clock. Typically, these biological functions display a pattern of activity and inactivity that is generally repeated approximately every 24 hours, oscillating between "active" and "inactive" states during the 24 hour period.

Thus, the present invention provides methods of regulating the activity of the circadian clock by administering to a mammal in need thereof a compound or pharmaceutical composition as disclosed herein. Generally, the regulation of the activity of the circadian clock is the result of the regulation of CLOCK:BMAL1, which is achieved according to the present methods by regulating the activity of SIRT1. The activity of SIRT1 is generally regulated according to the present methods by administration of a compound or pharmaceutical composition as disclosed herein, and in certain embodiments, by administration of a compound that affects the NAD+ pathway. The regulation of the circadian clock thereby permits regulation of activities mediated by the circadian clock.

According to the present invention, the activity of the circadian clock may be increased, decreased, or maintained by the administration of a compound or pharmaceutical composition as disclosed herein. Accordingly, biological functions (sometimes also referred to as biological activities) that are regulated by the activity of the circadian clock may also be increased, decreased, or maintained. In addition, these biological functions may also be time shifted; that is to say, an activity that typically occurs during a particular period, such as for example, during daytime or daylight hours (sometimes also referred to as the light cycle) or during the night or nighttime hours (sometimes also referred to as the dark cycle) may be shifted such that the activity occurs during the dark or light cycle, respectively, instead.

Pharmaceutical Formulations

The compounds of this invention are formulated with conventional carriers and excipients, which can be selected in accord with ordinary practice. Tablets can contain excipients, glidants, fillers, binders and the like. All formulations will optionally contain excipients such as those set forth in the "Handbook of Pharmaceutical Excipients" (1986). Suitable excipients are also listed in the US Food and Drug Administration Inactive Ingredients Database. Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations can range from about 3 to about 11, but is ordinarily about 7 to about 10.

While it is possible for the active ingredients to be administered alone, it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Formulations of the present invention suitable for oral administration may be presented as discrete units such as capsules, cachets or tablets, each containing a predetermined amount of the active ingredient as a powder or granules. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When intended for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques, including microencapsulation, to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active material(s) in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia; and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The amount of active ingredient that may be combined with the carrier material to produce a single dosage form will vary depending upon the subject treated and the particular mode of administration. For example, a time-release formulation intended for oral administration to humans may contain approximately 1 to approximately 1000 mg of active material compounded with an appropriate and convenient amount of carrier material which may vary from about 5% to about 95% of the total compositions (weight:weight). The pharmaceutical composition can be prepared to provide easily measurable amounts for administration.

Formulations suitable for intrapulmonary or nasal administration have a particle size for example in the range of about 0.1 to about 500 microns, such as about 0.5, about 1, about 30, or about 35 microns etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

INCORPORATION BY REFERENCE

All US patents and US and PCT published patent applications and non-patent literature mentioned in this specification are herein incorporated by reference to the same extent as if each independent patent and publication was specifically and individually indicated to be incorporated by reference.

EXAMPLES

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction condi- Preparation of bis(((2R,3S,4R,5R)-5-(3-carbamoylpyridin-1-ium-1-yl)-3,4-dihydroxytetrahydrofuran-2-yl)methyl) phosphate acetate

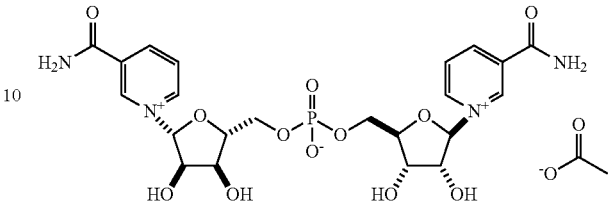

NR Triflate (5.00 g, 12.38 mmoles) was placed into a 100 ml 1-necked 24/40 round bottomed flask and placed under argon. The flask was put into a cold bath at −15 to −10° C., then trimethylphosphate (18 ml) was added and the reaction mixture stirred. Phosphorous oxychloride (0.865 mL, 1.42 gm, 9.28 mmoles, 0.75 eq) was added dropwise from a syringe over a 2 minute period. The reaction was stirred in this cold bath for 30 minutes and then placed into a refrigerator at 5° C. for 1-2 days. The reaction was then cooled to −15 to −10° C., and 1 to 6 eq. of water was added dropwise over 20 min. The reaction mixture was then placed onto an aminopropyl silica gel column and eluted with a gradient of ethyl acetate: 0.1M acetic acid in methanol: 0.1M acetic acid in water to give the desired product as its monoacetate salt. $^1$H NMR (500 MHz, D$_2$O) δ 9.43 (d, 2H J=0.6 Hz), 9.21 (dd, 2H, J=6.3, 1.1 Hz), 8.95 (ddd, 2H, J=8.1, 1.7, 1.2 Hz), 8.25 (td, 2H, J=7.2, 1.7 Hz), 6.18 (d, 2H, J=5.2 Hz), 4.57 (m, 2H), 4.48 (td, 2H, J=5.1, 2.1 Hz), 4.37 (m, 2H), 4.29 (ddd, 2H, J=12.0, 4.8, 2.4 Hz), 4.12 (ddd, 2H, J=12.0, 5.7, 2.7 Hz), 1.87 (s, 3H); $^{13}$C NMR (125 MHz, D$_2$O) δ 181.40, 165.66, 145.97, 142.45, 139.80, 134.00, 128.51, 99.72, 86.92, 77.57, 70.65, 64.64, 23.23; $^{31}$P NMR (200 MHz, D$_2$O), δ 0.74. (MS(ESI$^+$) m/z=571.1 (M$^+$).

tions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof. Unless noted otherwise, the starting materials for the synthesis described herein were obtained from commercial sources or known synthetic procedures and were used without further purification.

General Synthetic Scheme

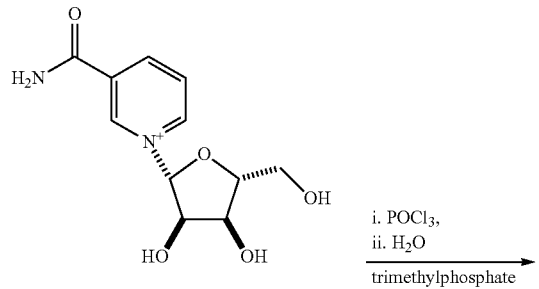

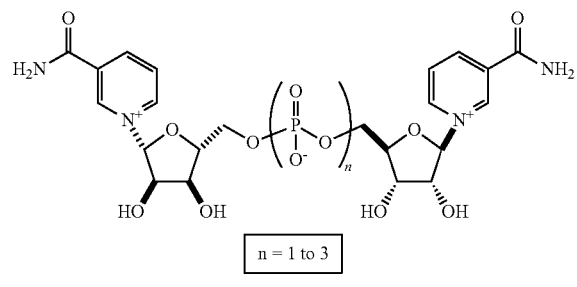

Preparation of Formula I, n=2

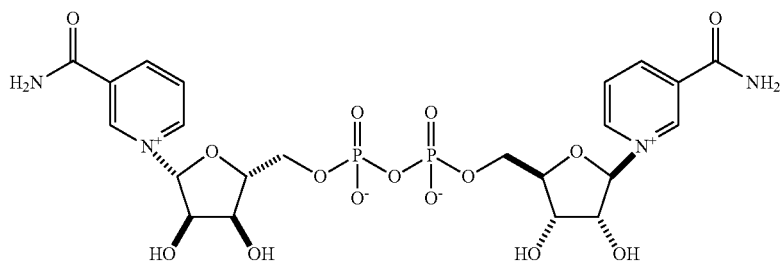

A 50 mL recovery flask was charged with 4.00 g (9.89 mmol) of nicotinamide riboside trifluoromethanesulfonate and a stir bar. The flask was purged with argon and capped with a septum. The flask was cooled with an ice bath, then 24 mL of trimethylphosphate was added via syringe. The mixture was stirred with ice cooling for 5-10 min, then 1.45 mL (15.56 mmol) of phosphorus oxychloride was added via syringe. After 3 h, 400 microliters of pyridine was added to the reaction. After 5.25 h, 534 microliters of water was added, dropwise over 1 min. Next, 3.2 mL of pyridine was added. The suspension was stirred with ice cooling for 1.5 h, then stored at 4° C. for 15.5 h.

The reaction was diluted with ethyl acetate until cloudy, then a small amount of methanol (about 1 mL) was added to give a clear solution. One half of the mixture was loaded onto a 90 g aminopropyl functionalized silica gel column (acetate form) that had been pre-equilibrated with ethyl acetate. The column was then eluted with a sequence of the following mobile phases: Mobile Phase A—ethyl acetate, Mobile Phase B: 0.1M acetic acid in methanol, Mobile Phase C: 0.1M acetic acid in water. The elution sequence was as follows (all ratios are v:v): 1000 mL of A, 50:50 A:B, 40:60 A:B, 100% B, 80:20 B:C, 60:40 B:C, 40:60 B:C, and 100% C. The product containing fractions were identified by HPLC MS (ESI$^+$, scan mode), with m/z=651 amu as the product mass. The product was mainly in the 60:40 B:C and 40:60 B:C fractions. The product containing fractions were pooled and concentrated in vacuo to a foam, then taken up in 0.5 mL of water and reconcentrated to a foam. The foam was dissolved in 3 mL of water, frozen, and lyophilized to give an impure product. The foam was re-purified via the same chromatography and lyophilization sequence to give the desired product as a white solid.

The second half of the crude product solution was then purified via the same sequence as the first half. This gave a second lot of the product as a white solid. The total yield of the combined lots was 50-500 mg.

The invention claimed is:

1. A composition comprising one or more pharmaceutically-acceptable solid excipients and one or more compounds having a structure represented by Formula II:

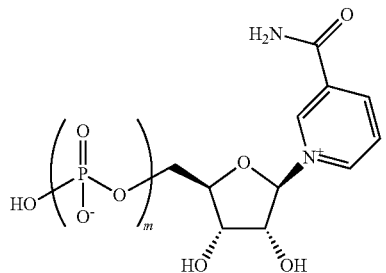

wherein m is 2 or 3, and/or salts thereof.

2. The composition of claim 1, wherein m is 2.

3. The composition of claim 1, wherein m is 3.

4. The composition of claim 1, wherein the pharmaceutically-acceptable solid excipient is selected from anti-adherent, binder, coating, dye, disintegrant, flavoring agent, glidant, lubricant, preservative, sorbent, sweetener, dispersant, diluent, filler, granulating agent, coating agent, wax, suspending agent, wetting agent, vehicle, and combinations thereof.

5. The composition of claim 1, wherein the composition is in a solid form selected from a tablet, a pill, a capsule, a caplet, a troche, granules, powders, a sachet, dry powder inhalation form, a chewable, a pastille, and alozenge.

6. The composition of claim 1, wherein the composition is in the form of a tablet.

7. The composition of claim 1, wherein the compound of Formula II is present in the composition in an amount from about 0.001% by weight to about 10% by weight.

8. The composition of claim 1, wherein the amount of the compound of Formula II in the composition is about 0.25% by weight of the composition.

9. The composition of claim 1, wherein the pharmaceutically acceptable excipient is present in an amount of at least about 5% by weight.

10. The composition of claim 1, wherein the pharmaceutically acceptable excipient is present in an amount of about 30% by weight.

11. A solid composition comprising one or more active pharmaceutical ingredients and a compound having a structure represented by Formula II:

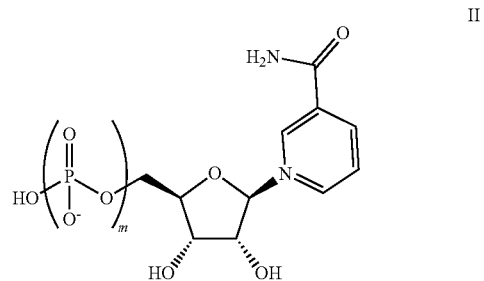

wherein m is 2 or 3, and/or a salt thereof.

12. The composition of claim 11, wherein m is 2.

13. The composition of claim 11, wherein m is 3.

14. The composition of claim 11, wherein the amount of the compound of Formula II relative to the amount of one or more active pharmaceutical ingredients ranges from about 0.001% by weight to less than about 50% by weight.

15. The composition of claim 11, wherein the amount of the compound of Formula II relative to the amount of one or more active pharmaceutical ingredients is from about 0.1% to about 1.5% by weight.

16. The composition of claim 11, wherein the one or more active pharmaceutical ingredients are selected from nicotinic acid (NA), nicotinamide (Nam), nicotinamide mononucleotide (NMN), nicotinamide riboside (NR), nicotinic acid mononucleotide (NaMN), nicotinic acid riboside (NAR), nicotinamide adenine dinucleotide (NAD$^+$/NADH), nicotinamide adenine dinucleotide phosphate (NADP), nicotinic acid adenine dinucleotide (NaAD), and combinations thereof.

17. A method of increasing NAD+ levels in a subject in need thereof, said method comprising administering a compound having the structure of Formula II:

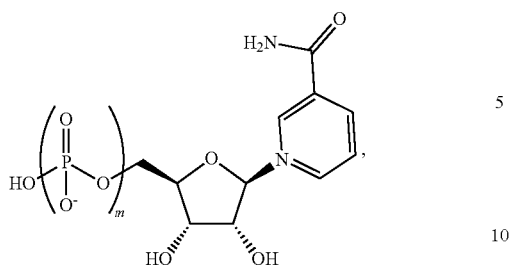

wherein m is 2 or 3,
or a salt thereof, or combinations thereof to said subject.

18. A method of increasing NAD+ levels in a subject in need thereof, said method comprising administering a composition according to claim 1 to said subject.

19. A method of increasing NAD+ levels in a subject in need thereof, said method comprising administering a composition according to claim 11 to said subject.

* * * * *